US006579673B2

(12) United States Patent
McGrath et al.

(10) Patent No.: US 6,579,673 B2
(45) Date of Patent: *Jun. 17, 2003

(54) PATTERNED DEPOSITION OF ANTIBODY BINDING PROTEIN FOR OPTICAL DIFFRACTION-BASED BIOSENSORS

(75) Inventors: Kevin McGrath, Alpharetta, GA (US); Rosann M. Kaylor, Cumming, GA (US); Dennis S. Everhart, Alpharetta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/213,713

(22) Filed: Dec. 17, 1998

(65) Prior Publication Data

US 2001/0055754 A1 Dec. 27, 2001

(51) Int. Cl.[7] .................... G01N 33/543; G01N 21/47; G01N 21/26

(52) U.S. Cl. .................... 435/5; 435/817; 435/176; 435/41; 435/7.21; 435/4; 435/6; 435/288; 435/291; 436/805; 436/525; 436/164; 436/807; 436/518; 250/461.1; 250/461.2; 422/55; 422/56; 422/57; 422/58; 422/69; 422/82.11; 427/169; 427/430.1; 427/162; 427/409; 427/410; 427/435; 205/777.5

(58) Field of Search .................... 436/805, 525, 436/164, 807, 528; 435/817, 176, 41, 7, 7.21, 4, 5, 6; 250/461.1, 461.2; 205/777.5; 422/55–57, 58, 69, 82.11; 7/180, 181, 182, 4, 28; 350/96.19; 264/212, 298; 427/169, 430.1, 162, 409, 410, 435

(56) References Cited

U.S. PATENT DOCUMENTS

| 4,312,228 A | 1/1982 | Wohltjen |
| 4,363,874 A | 12/1982 | Greenquist |
| 4,399,686 A | 8/1983 | Kindlund et al. |

(List continued on next page.)

FOREIGN PATENT DOCUMENTS

| EP | 0 453 820 | 10/1991 |
| EP | 0 596 421 A1 | 10/1993 |
| EP | 0 657 737 | 6/1995 |

(List continued on next page.)

OTHER PUBLICATIONS

B.D. Hames, Immuno–chemistry 1– A practical approach. Oxford University Press 1997, pp. 148 and 167.*
Abbott et al., Using Micromachining, Molecular Self-Assembly, and Wet Etching to Fabricate 0.1–1 $\mu$m–Scale Structures of Gold and Silicon, Chemistry of Materials, 6, No. 5, pp. 596–602 (1994).

(List continued on next page.)

Primary Examiner—Long V. Le
Assistant Examiner—Lisa V. Cook
(74) Attorney, Agent, or Firm—Kilpatrick Stockton LLP (57) ABSTRACT

The present invention provides an inexpensive and sensitive device and method for detecting and quantifying analytes present in a medium. The device comprises a metalized film upon which is printed a specific, predetermined pattern of an antibody-binding proteins. Upon attachment of a target analyte to select areas of the plastic film upon which the protein is printed, diffraction of transmitted and/or reflected light occurs via the physical dimensions and defined, precise placement of the analyte. A diffraction image is produced which can be easily seen with the eye or, optionally, with a sensing device.

52 Claims, 1 Drawing Sheet

U.S. PATENT DOCUMENTS

| | | | |
|---|---|---|---|
| 4,416,505 A | | 11/1983 | Dickson |
| 4,534,356 A | | 8/1985 | Papadakis |
| 4,561,286 A | | 12/1985 | Sekler et al. |
| 4,562,157 A | | 12/1985 | Lowe et al. |
| 4,596,697 A | | 6/1986 | Ballato |
| 4,661,235 A | | 4/1987 | Krull et al. |
| 4,690,715 A | | 9/1987 | Allara et al. |
| 4,776,944 A | | 10/1988 | Janata et al. |
| 4,812,221 A | | 3/1989 | Madou et al. |
| 4,837,715 A | | 6/1989 | Ungpiyakul et al. |
| 4,842,783 A | | 6/1989 | Blaylock |
| 4,844,613 A | | 7/1989 | Batchelder et al. |
| 4,851,816 A | | 7/1989 | Macias et al. |
| 4,877,747 A | | 10/1989 | Stewart |
| 4,895,017 A | | 1/1990 | Pyke et al. |
| 4,992,385 A | * | 2/1991 | Godfrey ..................... 436/525 |
| 5,023,053 A | | 6/1991 | Finlan |
| 5,035,863 A | | 7/1991 | Finlan et al. |
| 5,055,265 A | | 10/1991 | Finlan |
| 5,057,560 A | | 10/1991 | Mueller |
| 5,063,081 A | | 11/1991 | Cozzette et al. |
| 5,064,619 A | | 11/1991 | Finlan |
| 5,076,094 A | | 12/1991 | Frye et al. |
| 5,096,671 A | | 3/1992 | Kane et al. |
| 5,114,676 A | | 5/1992 | Leiner et al. |
| 5,134,057 A | | 7/1992 | Kuypers et al. |
| 5,143,854 A | | 9/1992 | Pirrung et al. |
| 5,152,758 A | | 10/1992 | Kaetsu et al. |
| 5,155,791 A | | 10/1992 | Hsiung |
| 5,182,135 A | | 1/1993 | Giesecke et al. |
| 5,189,902 A | | 3/1993 | Groeninger |
| 5,196,350 A | | 3/1993 | Backman |
| 5,235,238 A | | 8/1993 | Nomura et al. |
| 5,242,828 A | | 9/1993 | Bergstrom et al. |
| 5,268,306 A | | 12/1993 | Berger et al. |
| 5,280,548 A | | 1/1994 | Atwater et al. |
| 5,304,293 A | | 4/1994 | Tierney et al. |
| 5,327,225 A | | 7/1994 | Bender et al. |
| 5,334,303 A | | 8/1994 | Muramatsu et al. |
| 5,352,582 A | | 10/1994 | Lichtenwalter et al. |
| 5,369,717 A | | 11/1994 | Attridge |
| 5,374,563 A | | 12/1994 | Maule |
| 5,376,255 A | | 12/1994 | Gumbrecht et al. |
| 5,402,075 A | | 3/1995 | Lu et al. |
| 5,404,756 A | | 4/1995 | Briggs et al. |
| 5,415,842 A | | 5/1995 | Maule |
| 5,418,136 A | | 5/1995 | Miller et al. |
| 5,430,815 A | | 7/1995 | Shen et al. |
| 5,436,161 A | | 7/1995 | Bergstrom et al. |
| 5,451,683 A | | 9/1995 | Barrett et al. |
| 5,455,475 A | | 10/1995 | Josse et al. |
| 5,482,830 A | | 1/1996 | Bogart et al. |
| 5,482,867 A | | 1/1996 | Barrett et al. |
| 5,489,678 A | | 2/1996 | Fodor et al. |
| 5,489,988 A | | 2/1996 | Ackley et al. |
| 5,492,840 A | | 2/1996 | Malmqvist et al. |
| 5,510,481 A | | 4/1996 | Bednarski |
| 5,512,131 A | * | 4/1996 | Kumar et al. ............ 156/655.1 |
| 5,514,501 A | | 5/1996 | Tarlov |
| 5,514,559 A | | 5/1996 | Markert-Hahn et al. |
| 5,527,711 A | | 6/1996 | Tom-Moy et al. |
| 5,554,541 A | | 9/1996 | Malmqvist et al. |
| 5,568,606 A | | 10/1996 | Dobbek |
| 5,580,697 A | | 12/1996 | Keana et al. |
| 5,620,850 A | | 4/1997 | Bamdad et al. |
| 5,624,537 A | * | 4/1997 | Turner et al. ............... 204/403 |
| 5,643,681 A | | 7/1997 | Voorhees et al. |
| 5,658,443 A | | 8/1997 | Yamamoto et al. |
| 5,972,199 A | * | 10/1999 | Heller et al. ............. 205/777.5 |
| 6,060,256 A | * | 5/2000 | Everhart et al. ........... 435/7.21 |

FOREIGN PATENT DOCUMENTS

| | | | | |
|---|---|---|---|---|
| GB | 2273772 | 6/1994 | | |
| WO | 90/05305 | 5/1990 | | |
| WO | 91/05999 | 5/1991 | | |
| WO | WO 96/24062 | * 8/1996 | ......... | G01N/33/543 |
| WO | 96/26435 | 8/1996 | | |
| WO | 96/29629 | 9/1996 | | |
| WO | WO 96/29629 | * 9/1996 | | |
| WO | 96/33971 | 10/1996 | | |
| WO | 98/10334 | 3/1998 | | |
| WO | WO 98/27417 | * 6/1998 | .......... | G01N/21/47 |
| WO | WO 98/43086 | * 10/1998 | ......... | G01N/33/543 |

OTHER PUBLICATIONS

Bhatia, S.K. et al., "Fabrication of Surfaces Resistant to Protein Adsorption and Application to Two–Dimensional Protein Patterning," Analytical Biochem., vol. 208, p. 197–205, 1993.

Bhatia, S.K. et al., "New Approach to Producing Patterned Biomolecular Assemblies," 1992, J. Am. Chem. Soc., vol. 114, p. 4432.

Burton et al. "Prediction of Segregation to Alloy Surfaces from Bulk Phase Diagram", Phys. Rev. Letter, vol. 37, No. 21, pp. 1433–1436 (Nov. 22, 1976).

Copy of Search Report for PCT/US97/08522 dated Aug. 8, 1997.

Dahint et al., "Probing of strong and weak electrolytes with acoustic wave fields", Sensors and Actuators B, vol. 9, pp. 155–162 (1992).

Diamandis, EP et al., "The Biotin–(Strept)Avidin System: Principles and Applications in Biotechnology," Clin. Chem., vol. 37(5), 1991, p. 625–636.

Folkers et al., "Self–Assembled Monolayers of Long–Chain Hydroxamic Acids on the Native Oxides of Metals", Langmuire, vol. 11, No. 3, pp. 813–824 (1995).

Häussling, L. et al., "Direct Observation of Streptavidin Specifically Adsorbed on Biotin–Functionalozed Self–Assembled Monolayers with the Scanning Tunneling Microscope," Angew. Chem. Int. Ed. Engl., vol. 30, No. 5, 1991, p. 569–572.

Irie, M. "Stimuli–Responsive Poly(N–isopropylacrylamide) Photo– and Chemical–Induced Phase Transitions", Advances in Polymer Science, vol. 110, pp. 49–65 (1993).

Jennane, J. et al., "Photolithography of self–assembled monolayers: optimization of protecting groups by an electroanalytical method," Can. J. Chem. vol. 74, 1996, p. 2509–2517.

Jeon et al., "Patterned Self–Assembled Monolayers Formed by Microcontact Printing Direct Selective Metalization by Chemical Vapor Deposition on Planar and Nonplanar Substrates", Langmuir, vol. 11, No. 8, pp. 3024–3026 (1995).

Johnson et al. "Orientation dependence of surface segregation in a dilute Ni–Au alloy", J. Vac. Sci. Technol., vol. 15, No. 2, pp. 467–469 (Mar./Apr. 1978).

Josse et al., "Electrical Surface Perturbation of a Piezoelectric Acoustic Plate Mode by a Conductive Liquid Loading", IEEE Transactions on Ultrasonics, Ferroelectrics, and Frequency Control, vol. 39, No. 4, (Jul. 1992).

Josse et al., "On the use of ZX–LiNbO3 acoustic plate mode devices as detectors for dilute electrolytes", Sensors and Actuators B, vol. 9, pp. 97–112 (1992).

Kelkar et al., "Acoustic Plate Waves for Measurement of Electrical Properties of Liquids", Microchem. Journal, vol. 43, pp. 155–164 (1991).

Kim et al., "Combining Patterned Self–Assembled Monolayers of Alkanethiolates on Gold with Anisotropic Etching of Silicon to Generate Controlled Surface Morphologies", J. Electrochem. Soc., vol. 142, No. 2, pp. 628–633 (Feb. 1995).

Kokufuta, E. "Novel Applications for Stimulus–Sensitive Polymer Gels in the Preparation of Functional Immobilized Biocatalysts", Advances in Polymer Science, vol. 110, pp. 157–177 (1993).

Kumar et al., "Features of gold having micrometer to centimeter dimensions can be formed through a combination of stamping with an elastomeric stamp and an alkanethiol "ink" following by chemical etching", Appl. Phys. Lett., vol. 63, pp. 2002–2004 (1993).

Kumar et al., "Patterned Condensation Figures as Optical Diffraction Gratings", Science, vol. 263, pp. 60–62 (Jan. 7, 1994).

Kumar et al., "Patterning Self–Assembled Monolayers: Applications in Materials Science", Langmuir, vol. 10, pp. 1498–511 (1994).

Larsen N.B. et al., "Order in Microcontact Printed Self–Assembled Monolayers", J. Am. Chem. Soc. vol. 119, pp. 3017–3026, 1997.

Liedberg et al., "Molecular Gradients of ω–Substituted Alkanethiols on Gold: Preparation and Characterization", Langmuir, vol. 11, pp. 3821–3827 (1995).

Mrksich et al., "Biospecific Adsorption of Carbonic Anhydrase to Self–Assembled Monolayers of Alkanethiolates That Present Benzenesulfonamide Groups on Gold," J. American Chem. Soc., vol. 117, pp. 12009–10 (1995).

Mrksich et al., "Patterning self–assembled monolayers using microcontact printing: A new technology for biosensors?", Tibtech, vol. 13, pp. 228–235 (1995).

Muller, W. et al., Science, vol. 262, Dec. 10, 1993, p. 1706–1708.

Okano, T. "Molecular Design of Temperature–Responsive Polymers as Intelligent Materials", Advances in Polymer Science, vol. 110, pp. 179–197 (1993).

Osada et al, "Stimuli–Responsive Polymer Gels and Their Application to Chemomechanical Systems", Prog. Polym. Sci., vol. 18, pp. 187–226 (1993).

Osada et al., "Intelligent Gels", Scientific American, pp. 82–87, May 1993.

R. Block et al., "Mechanical resonance gas sensors with piezoelectric excitation and detection using PVDF polymer foils", Sensors and Actuators, vol. B7, Mar. 1992, pp. 596–601.

Responsive Gels: vol. Transitions I, vol. 109: Advances in Polymer Science, Dusek, K. ed., Springer–Verlag, Berlin, 1993.

Responsive Gels: vol. Transitions II, vol. 110: Advances in Polymer Science, Dusek, K. ed., Springer–Verlag, Berlin, 1993.

S.J. Martin, "Sensing liquid properties with thickness–shear mode resonators", Sensors and Actuators A, vol. A44, Sep. 1994, pp. 209–218.

Saito et al., "Volume Phase Transition of N–Alkylacrylamide Gels", Advances on Polymer Science, vol. 109, pp. 207–232 (1993).

Seah, M.P. "Quantitative Prediction of Surface Segregation", Journal of Catalysis, vol. 57, pp. 450–457 (1979).

Shana et al, "Analysis of electrical equivalent circuit of quartz crystal resonator loaded with viscous conductive liquids", Journal of Electroanalytical Chemistry, vol. 379, pp. 21–33 (1994).

Shana et al., "Quartz Crystal Resonators as Sensors in Liquids Using the Acoustoelectric Effect", Anal. Chem., vol. 66, pp. 1955–1964 (1994).

Shibayama et al., "Volume Phase Transition and Related Phenomena of Polymer Gels", Advances in Polymer Science, vol. 109, pp. 1–62 (1993).

Tsai et al., "Comment on the Prediction of Segregation to Alloy Surfaces", Journal of Catalysis—Letters to the Editor, vol. 50, pp. 200–202 (1977).

Wilbur et al., "Microfabrication by Microcontact Printing of Self–Assembled Monolayers", Adv. Mater., vol. 6, No. 7/8, pp. 600–604 (1994).

Moffat, T.P., et al., "Patterned Metal Electrodeposition Using an Alkanethiolate Mask" J. Electrochem Soc., vol. 142, No. 11, pp. 220–221 (Nov. 1995).

Dobisz, Elizabeth, A.. et al., "Self–Assembled Monolayer Films for Nanofabrication", Mat. Res. Soc. Symp. Proc., vol. 380, pp. 23–33 (1995).

Laibinis, Paul, E., et al., "Comparison of the Structures and Wetting Properties of Self–Assembled Monolayers on n–Alkanethiols on the Coinage Metal Surfaces, Cu, Ag, Aul", Amer. Chem., Soc., vol. 113, No. 19, pp. 7152–7167 (1991).

Abbott, Nicholas, L., "Manipulation Substratum Adhesiveness: A Model for Morphogenetic Cues Controlling Cell Behavior", Exp. Cell Res., vol. 198, pp. 124–129(1992).

Tiberio, R.C., et al., "Self–Assembled Monolayer Electron Beam Resist on GaAs", Amer. Inst. Phys., (Feb. 1993).

Biebuyck, Hans, A., et al., "Self Organization of Organic Liquids on Patterned Self–Assembled Monolayers of Alkanethiolates on Gold", Langmuir, vol., 10, No. 8, pp. 2790–2793 (1994).

Gorman, Christopher, B., et al., "Use of a Patterned Self–Assembled Monolayer to Control the Formation of a Liquid Resist Pattern on a Gold Surface", Chem. Mater., vol. 7, No. 2, pp. 252–254 (1995).

Kumar, Amit, et al., "The Use of Self–Assembled Monolayers and a Selective Etch to Generate Patterned Gold Features", Am. Chem. Soc., pp. 9188–9189 (1992).

Tarlov, Michael, J., et al., "UV Photopatterning of Alkanethiolate Monolayers Self–Assembled on Gold and Silver", J. Am. Chem. Soc., vol. 11, No. 12, pp. 5305–5306 (1993).

Whitesides, George, M., et al, "Wet Chemical Approaches to the Characterization of Organic Surfaces: Self Assembled Monolayers, Wetting, and the Physical–Organic Chemistry of the Solid Liquid Interface", Langmuir, vol. 6, pp. 87–96 (1990).

Gorman, Christopher, B., et al., "Fabrication of Patterned, Electrically Conducting Polyprrole Using a Self–Assembled Monolayer: A Route to All Organic Circuits", Chem. Mater., vol. 7, No. 3, pp. 526–529 (1995).

Gorman, Christopher, B., et al., "Control of the Shape of Liquid Lenses on a Modified Gold Surface Using an Applied Electrical Potential Across a Self Assembled Monolayer", Langmuir, vol. 11, No. 6, pp. 2242–2246 (1995).

Dressick, Walter, J., et al., "Photopatterning and Selctive Electrodes Metalization of Surface–Attached Ligands", Chem. Mat., vol. 3, pp. 149–150 (1993).

Kang, Doris, et al., "Patterned Functionalization of Gold and Single Crystal Silicon via Photochemical Reaction of Surface–Confined Derivatives of ($n^5$–C5H5)Mn($CO^3$", Langmuir, vol. 7, No. 10, pp. 2169–2174 (1991).

Lercel, M.J., et al., "Pattern Transfer of Electron Beam Modified Self–Assembled Monolayers for High–Resolution Lithography", J. Vac. Sci. Techn., vol. 13, No. 3, pp. 1139–1143 (1995).

Rozsnyai, Lawrence, F., et al., "Selective Electrochemical Deposition of Polyaniline via Photopatterning of a Monolayer–Modified Substrate", J.Am. Chem. Soc., vol. 116, pp. 5993–5994 (1994).

Sondag–Huethorst, J.A.M., et al., "Generation of Electrochemicaly Deposited metal Patterns by Means of Electro Beam (nano)lithography of Self–Assembled Monolayer Resists", Appl. Phys. Lett., vol. 64, pp. 285–287 (1994).

Wollman, Eric, W., et al. Photosensitive Self–Assembled Monolayers on Gold: Photochemistry of Surface–Confined Aryl Azide and Cyclopentadienylmanganese Tricarbonyl, J. Am. Chem. Soc., vol. 116, No. 10, pp. 4395–4404 (1994).

Xia, Younan, et al., "Microcontact Printing of Octadecylsiloxane on the Surface of Silicon Dioxide and its Application in Microfabrication", Am. Chem. Soc., pp. 9576–9577 (1995).

Erbach, R., et al, "Application of rod–like polymers with ionophores as Langmuir–Blodgett membranes for Si–based ion sensors", Sensors and Actuators, B., vol. 6, pp. 211–216 (1992).

Miller, D.L.., "Preparation and Characterization of ultrathin Pb and In films on PbTe and Te", J. Vac. Sci. Technol., vol. 13, No. 6 (1976).

Abbott, N.L. "Manipulation of the Wettability of Surfaces on the .01 to 1–Micrometer Scale Through Micromachining and Molecular Self Assembly", Science, vol. 257 (Sep. 1992).

International Search Report.

* cited by examiner

Fig_1

Fig_2

US 6,579,673 B2

PATTERNED DEPOSITION OF ANTIBODY BINDING PROTEIN FOR OPTICAL DIFFRACTION-BASED BIOSENSORS

TECHNICAL FIELD

The present invention is generally in the field of detecting analytes in a medium and, more particularly, the present invention relates to micro-contact printing of antibody-binding proteins onto a substrate for the development of single use, disposable sensors to indicate the presence of the analyte in a medium.

BACKGROUND OF THE INVENTION

There are many systems and devices available for detecting a wide variety of analytes in various media. Most of these systems and devices are relatively expensive and require a trained technician to perform the test. There are many cases where it would be advantageous to be able to rapidly and inexpensively determine if an analyte were present. What is needed is a biosensor system that is easy and inexpensive to manufacture and is capable of reliable and sensitive detection of analytes, including smaller analytes. Additionally, what is needed is an easy flexible method of preparation of the biosensors which would permit optimum scale-up processing.

Sandstrom et al., 24 *Applied Optics* 472, 1985, describe use of an optical substrate of silicon with a layer of silicon monoxide and a layer of silicon formed as dielectric films. They indicate that a change in film thickness changes the properties of the optical substrate to produce different colors related to the thickness of the film. The thickness of the film is related to the color observed and a film provided on top of an optical substrate may produce a visible color change. The authors indicate that a mathematical model can be used to quantitate the color change, and that "[c]alculations performed using the computer model show that very little can be gained in optical performance from using a multi-layer structure . . . but a biolayer on the surface changes the reflection of such structures very little since the optical properties are determined mainly by the interfaces inside the multilayer structure. The most sensitive system for detection of biolayers is a single layer coating, while in most other applications performance can be by additional dielectric layers."

Sandstrom et al., go on to indicate that slides formed from metal oxides on metal have certain drawbacks, and that the presence of metal ions can also be harmful in many biochemical applications. They indicate that the ideal top dielectric film is a 2–3 nm thickness of silicon dioxide which is formed spontaneously when silicon monoxide layer is deposited in ambient atmosphere, and that a 70–95 nm layer silicon dioxide on a 40–60 nm layer of silicon monoxide can be used on a glass or plastic substrate. They also describe formation of a wedge of silicon monoxide by selective etching of the silicon monoxide, treatment of the silicon dioxide surface with dichlorodimethylsilane, and application of a biolayer of antigen and antibody. From this wedge construction they were able to determine film thickness with an ellipsometer, and note that the "maximum contrast was found in the region about 65 nm where the interference color changed from purple to blue." They indicate that the sensitivity of such a system is high enough for the detection of protein antigen by immobilized antibodies. They conclude "the designs given are sensitive enough for a wide range of applications. The materials, i.e., glass, silicon, and silicon oxides, are chemically inert and do not affect the biochemical reaction studied. Using the computations above it is possible to design slides that are optimized for different applications. The slides can be manufactured and their quality ensured by industrial methods, and two designs are now commercially available.

U.S. Pat. No. 5,512,131 issued to Kumar et al. describes a device that includes a polymer substrate having a metal coating. An antibody-binding protein layer is stamped on the coated substrate. The device is used in a process for stamping or as a switch. A diffraction pattern is generated when an analyte binds to the device. A visualization device, such as a spectrometer, is then used to determine the presence of the diffraction pattern.

However, the device described by Kumar et al. has several disadvantages. One disadvantage is that an extra visualization device is needed to view any diffraction pattern. By requiring a visualization device, the Kumar et al. device does not allow a large number of samples to be tested since it is not possible to determine the presence of an analyte by using the unaided eye.

U.S. Pat. No. 5,482,830 to Bogart, et al., describes a device that includes a substrate which has an optically active surface exhibiting a first color in response to light impinging thereon. This first color is defined as a spectral distribution of the emanating light. The substrate also exhibits a second color which is different from the first color (by having a combination of wavelengths of light which differ from that combination present in the first color, or having a different spectral distribution, or by having an intensity of one or more of those wavelengths different from those present in the first color). The second color is exhibited in response to the same light when the analyte is present on the surface. The change from one color to another can be measured either by use of an instrument, or by eye. Such sensitive detection is an advance over the devices described by Sandstrom and Nygren, supra, and allow use of the devices in commercially viable and competitive manner.

However, the method and device described in the Bogart, et al. patent has several disadvantages. One disadvantage is the high cost of the device. Another problem with the device is the difficulty in controlling the various layers that are placed on the wafer so that one obtains a reliable reading. What is needed is a biosensor device that is easy and inexpensive to manufacture and is capable of reliable and sensitive detection of the analyte to be detected.

SUMMARY OF THE INVENTION

The present invention provides an inexpensive and sensitive device and method for detecting analytes present in a medium. The device comprises a biosensing device having a substrate, preferably a metalized polymer film, upon which is printed a specific predetermined pattern of antibody-binding proteins such as Protein A or Protein G. Subsequent exposure to the antibody specific for the desired analyte results in patterned deposition of this antibody. Overall, this allows a modular production format such that large rolls of patterned protein may be made for use with different analytes. Then as needed, the final product may be made by exposure to the necessary antibody.

Upon attachment of a target analyte, which is capable of scattering light, to select areas of the polymer film upon which the protein and antibody are patterned, diffraction of transmitted and/or reflected light occurs via the physical dimensions and defined, precise placement of the analyte. A diffraction image is produced which can be easily seen with the eye or, optionally, with a sensing device.

The present invention utilizes methods of contact printing of patterned, antibody-binding proteins. These proteins bind to antibodies to pattern them on the surface as well as maintain the optimum orientation for the receptor antibodies. The receptor antibodies are specific for a particular analyte or class of analyte, depending upon the protein used. Methods of contact printing which would be useful in generating the sensing devices used in the present system are disclosed fully in U.S. patent application Ser. Nos. 08/707,456, now U.S. Pat. No. 6,020,047 and 08/769,594, now U.S. Pat. No. 6,048,623, both of which are incorporated herein by reference in their entirety. However, since these methods relate to self-assembling monolayers, the methods need to be altered slightly, as discussed below, to print the antibody-binding protein material as this material is not self-assembling.

Patterned antibody-binding protein layers with bound antibodies cause patterned placement or binding of analytes thereon. The biosensing devices of the present invention produced thereby may be used in one of two ways, depending on the size of the analyte. For analytes which are capable of causing diffraction by themselves, such as microorganisms, the system is used by first exposing the biosensing device to a medium that contains the analyte of choice and then, after an appropriate incubation period, transmitting a light, such as a laser, through the film or reflecting it off of the film. If the analyte is present in the medium and is bound to the antibodies on the patterned antibody-binding protein layer, the light is diffracted in such a way as to produce a visible image.

Optionally, for very small analytes such as proteins, the system may utilize "diffraction enhancing elements" which are capable of binding to the target analyte and to the biosensor and are capable of producing a substantial change in the height and/or refractive index, thereby increasing the diffraction efficiency of the biosensor and permitting the detection of smaller analytes. In use, a target analyte attaches either to the diffraction enhancing element, which then attaches to the biosensor, or directly to select areas of the polymer film upon which the protein and antibody are printed. Then diffraction of transmitted and/or reflected light occurs via the physical dimensions and defined, precise placement of the analyte. A diffraction image is produced which can be easily seen with the eye or, optionally, with a sensing device.

Another option for use of this sensor involves the detection of analytes which are antibodies. The sensing device could comprise only the patterned antibody-binding proteins, and then would be exposed to the medium plus diffraction enhancing particles which have an antibody specific to the antibody to be detected. The selection of the antibody on the particle is preferably made so that it does not bind nonspecifically to the patterned antibody-binding protein, but instead binds only when the analyte antibody is also bound. In this way, the diffraction enhancing elements would cause a substantial change in the height and/or refractive index if the analyte antibody is present, thereby causing a diffraction image to form. It is envisioned that the same format could be used with other immunoassay formats, such as lateral flow assays or microwell plates."

In other words, the antibody-binding protein and antibody layers with the analyte bound thereto can produce optical diffraction patterns to indicate the presence of the analyte. The light can be in the visible spectrum, and be either reflected from the film, or transmitted through it, and the analyte can be any compound or particle reacting with the antibody-binding protein layer. The light can be a white light or monochromatic electromagnetic radiation in the visible region. The present invention also provides a flexible support for an antibody-binding protein layer on gold or other suitable metal or metal alloy.

The present invention provides a low-cost, disposable biosensor which can be mass produced. It includes the use of surfaces patterned with an antibody-binding protein. Typically, these proteins bind an antibody by its constant region ($F_c$) so that the antibody's antigen-binding regions ($F_{ab}$) are free for optimum binding activity. The preparation of the patterned protein surfaces also allows maximum flexibility in the sensor production. The final step in production, capturing the desired antibody in the patterned areas, may be done as needed for the desired analyte (i.e. at the time of manufacture).

The biosensors of the present invention can be produced as a single test for detecting an analyte or it can be formatted as a multiple test device. The biosensors of the present invention can be used to detect contamination in garments, such as diapers, and to detect contamination by microorganisms.

The present invention can also be used on contact lenses, eyeglasses, window panes, pharmaceutical vials, solvent containers, water bottles, adhesive bandages, and the like to detect contamination.

These and other features and advantages of the present invention will become apparent after a review of the following detailed description of the disclosed embodiments.

DETAILED DESCRIPTION

The present invention features improved biosensing devices, and methods for using such biosensing devices, for detecting and quantifying the presence or amount of an analyte of interest within a medium. The analytes that can be detected by the present invention include, but are not limited to, microorganisms such as bacteria, yeasts, fungi and viruses. In contrast to prior devices, those of the present invention allow detection of extremely small quantities of analyte in a medium in a rapid assay lasting only a few minutes. In addition, no signaling or associated electronic components are required in the biosensing devices of the present invention.

The present invention comprises micro-contact printing of antibody-binding proteins onto a polymer film, which may also have a metal coating. This allows an easy, modular method of production in that subsequent exposure to an antibody causes its patterned binding. In addition, these proteins may enhance the activity of the immobilized antibody. The present invention allows for the development of single use, disposable biosensors based on light diffraction to indicate the presence of the analyte. Upon attachment of a target analyte to select areas of the plastic film which contain the protein, diffraction of transmitted and/or reflected light occurs via the physical dimensions and defined, precise placement of the analyte. For example, yeast, fungi or bacterium are large enough to act as diffraction elements for visible light when placed in organized patterns on a surface. Additionally, the present invention may include diffraction enhancing elements which increase the diffraction efficiency of the biosensor, thereby making it possible to detect any number of different analytes. In addition to producing a simple diffraction image, patterns of analytes can be such as to allow for the development of a holographic sensing image and/or a change in visible color. Thus, the appearance of a hologram or a change in an existing hologram will indicate a positive response. The pattern made by the diffraction of the transmitted light can be any shape including, but not limited to, the transformation of a pattern from one pattern to another upon binding of the analyte to the receptive material. In particularly preferred embodiments, the diffraction pattern is discernible in less than one hour after contact of the analyte with the biosensing device of the present invention.

The diffraction grating which produces the diffraction of light upon interaction with the analyte preferably has a minimum periodicity of the wavelength and a refractive index different from that of the surrounding medium. Very small analytes, such as viruses or molecules, can be detected indirectly by using a larger particle that is specific for the small analyte. In one embodiment in which the small analyte can be detected comprises coating the particle, such as a latex bead, with a protein material that specifically binds to the analyte of interest. Particles that can be used in the present invention include, but are not limited to, glass, cellulose, synthetic polymers or plastics, latex, polystyrene, polycarbonate, proteins, bacterial or fungal cells and the like. The particles are preferably spherical in shape, but the structural and spatial configuration of the particles is not critical to the present invention. For instance, the particles could be slivers, ellipsoids, cubes, and the like. A desirable particle size ranges from a diameter of approximately 0.2 $\mu$m to 50.0 $\mu$m, desirably between approximately 0.4 $\mu$m to 1 $\mu$m.

The composition of the particle is not critical to the present invention.

The antibody which is immobilized/patterned on the surface will specifically bind to an epitope on the analyte that is different from the epitope used in the binding to the diffraction enhancing element. Thus, for detecting a medium with a small analyte, such as viral particles, the medium is first exposed to the diffraction enhancing element particles, such as latex particles, to which the viral particles bind. Then, the diffraction enhancing element particles are optionally washed and exposed to the polymer film with the antibody-binding protein layers containing the virus specific antibodies. The antibodies then bind to the viral particles on the element particle thereby immobilizing the element particles in the same pattern as the antibodies on the film. Because the bound element particles will cause diffraction of the visible light, a diffraction pattern is formed, indicating the presence of the viral particle in the liquid. Additionally, the polymer film may include a metal coating thereon. The antibody-binding protein layer would then be located on the metalized surface of the film.

Alternatively, the analyte may be detected by first exposing the substrate to the medium containing the analyte and causing the analyte to bind to the antibody-binding protein layer material containing the analyte-specific antibody. Next, a solution containing the diffraction enhancing element particles is contacted with the substrate having the analyte bound thereto. The particles then bind to the analyte. Because the bound element particles will cause diffraction of the visible light, a diffraction pattern is formed, indicating the presence of the analyte in the liquid.

Finally, in a preferred embodiment, the biosensor, the diffraction enhancing element particles and the medium containing the analyte may be admixed simultaneously. This will result in a combination of the binding procedures discussed above. Some of the analytes will first bond with a diffraction enhancing element particle prior to binding to the substrate. Other analytes will first bind with the substrate and then bind with an element particle. When a point-light source is shown through the sensor, a diffraction pattern is formed, indicating the presence of the analyte in the liquid.

The analytes that are contemplated as being detected using the present invention include, but are not limited to, bacteria; yeasts; fungi; viruses; rheumatoid factor; antibodies, including, but not limited to IgG, IgM, IgA and IgE antibodies; carcinoembryonic antigen; streptococcus Group A antigen; viral antigens; antigens associated with autoimmune disease; allergens; tumor antigens; streptococcus Group B antigen; HIV I or HIV II antigen; or host response (antibodies) to these and other viruses; antigens specific to RSV or host response (antibodies) to the virus; an antigen; enzyme; hormone; polysaccharide; protein; lipid; carbohydrate; drug or nucleic acid; Salmonella species; Candida species, including, but not limited to *Candida albicans* and *Candida tropicalis*; Salmonella species; *Neisseria meningitides* groups A, B, C, Y and W sub 135, *Streptococcus pneumoniae, E. coli* K1, *Haemophilus influenza* type B; an antigen derived from microorganisms; a hapten, a drug of abuse; a therapeutic drug; an environmental agent; and antigens specific to hepatitis.

In another embodiment of the present invention, nutrients for a specific class of microorganisms can be incorporated into the antibody-binding protein layer. In this way, very low concentrations of microorganisms can be detected by first contacting the biosensor of the present invention with the nutrients incorporated therein and then incubating the biosensor under conditions appropriate for the growth of the bound microorganism. The microorganism is allowed to grow until there are enough organisms to form a diffraction pattern. Of course, in some cases, the microorganism can multiply enough to form a diffraction pattern without the presence of a nutrient on the patterned monolayer.

A part of the present invention is the method used to pattern receptors such as antibodies onto a polymer film or a metalized polymer film. The method entails microcontact printing proteins that bind to antibodies. These proteins can include, but are not limited to, Protein A, Protein G, Protein L, as well as their recombinant forms. Commercial versions, such as Zymed's (San Francisco, Calif.) KAPPALOCK™, are also suitable. Thus, the protein material is defined as the base material to create a specific binding pair, with the other part comprising an antibody specific to the analyte of interest.

The receptor material that is bound to the patterned protein is characterized by an ability to specifically bind the analyte or analytes of interest. Whatever the selected analyte of interest is, the protein material is designed to bind specifically with the analyte of interest. In the preferred embodiments, the biosensing device is configured and arranged to provide a pattern detectable by eye in response to transmission of polychromatic light when the analyte of interest is sandwiched between the antibody and a diffraction enhancing element. In another embodiment, where the analyte is large enough to diffract light, no diffraction enhancing element may be needed.

In many instances, a "blocker" may be necessary to prevent non-specific binding. The term "blocker" as used herein means a reagent that adheres to the sensor surface so that it "blocks" or prevents non-analyte materials from nonspecifically binding to the surface (either in the patterned or un-patterned areas). The blocking step may be done as a post-treatment to a surface which has already been contact printed ("post-block"), and is the standard technique for filling in non-contact printed regions with another thiol. However, the inventors have discovered that a "pre-block" technique is preferred over the post-block technique. In the pre-block technique, the surface of the substrate is pre-treated with a non-thiol containing blocker and then contact printed. Not wishing to be bound to any theory, it is theorized that the contact printed material (usually sulfur containing) displaces the physisorbed blocker, thereby permitting the antibody-binding protein material to be bound directly to the surface of the substrate. A subsequent post-block may also be performed, if desired. Blockers can include, but are not limited to, casein, albumins such as bovine serum albumin, pluronic or other surfactants, polyethylene glycol, polyvinyl alcohol, or sulfur derivatives of the above compounds, and any other blocking material known to those of ordinary skill in the art.

The matrix containing the analyte of interest may be a solid, a gas, or a bodily fluid such as an interstitial fluid, mucous, saliva, urine, fecal material, tissue, marrow, cerebral spinal fluid, serum, plasma, whole blood, synovial sputum, buffered solutions, extracted solutions, semen, vaginal secretions, pericardial, gastric, peritoneal, pleural, a throat swab or other washes and the like. The analyte of interest may be an antigen, an antibody, an enzyme, a toxin, an environmental agent, a cytoplasm component, pili or flagella component, protein, polysaccharide, drug, or any other material that is capable of being recognized by an antibody. For example, receptor material for bacteria may specifically bind a surface membrane component, protein or lipid, a nucleic acid, or an enzyme. The analyte which is indicative of the bacteria may be a saccharide or polysaccharide, an enzyme, a nucleic acid, a membrane component, a ganglioside or an antibody produced by the host in response to the bacteria. The presence of the analyte may indicate an infectious disease (bacterial or viral), cancer, an allergy, or other medical disorder or condition. The presence of the analyte may be an indication of water or food contamination or other harmful materials. The analyte may indicate drug abuse or may monitor levels of therapeutic agents.

In some cases, the analyte may not simply bind the receptor material, but may cause a detectable modification of the receptor material to occur. This interaction could cause an increase in mass at the test surface or a decrease in the amount of receptor material on the test surface. An example of the latter is the interaction of a degradative enzyme or material with a specific, immobilized substrate. In this case, one would see a diffraction pattern before interaction with the analyte of interest, but the diffraction pattern would disappear if the analyte were present. The specific mechanism through which binding, hybridization, or interaction of the analyte with the receptor material occurs is not important to this invention, but may impact the reaction conditions used in the final assay protocol.

In general, the antibody-binding protein may be passively adhered to the substrate layer. If required, functional groups may be conjugated onto the antibody-binding protein to allow its covalent attachment onto the test surface.

A wide range of techniques can be used to apply the protein material to the substrate. Test surfaces may be coated with antibody-binding protein by application of solution in discrete arrays or patterns; spraying, ink jet, or other imprinting methods; or by contact printing. The technique selected should minimize the amount of protein material required for coating a large number of test surfaces and maintain the stability/functionality of protein material during application. The technique must also apply or adhere the protein material to the substrate in a very uniform and reproducible fashion.

The next step would comprise exposing the patterned surface to the antibody specific for the desired analyte. This could be done by total immersion in a solution for a predetermined period of time, spraying, or spin coating. In addition, controlled placement of various antibodies could lead to a multi-analyte system. Another advantage to this process is the modular format for production. In other words, one system with patterned antibody-binding protein can be optimized and then provide detection of a wide variety of analytes, depending on the antibody bound.

The medium in which the analyte may reside can be solid, gel-like, liquid or gas. For purposes of detecting an analyte in a body fluid, the fluid is selected from, but not limited to, urine, serum, plasma, spinal fluid, sputum, whole blood, saliva, uro-genital secretions, fecal extracts, pericardial, gastric, peritoneal, pleural washes, vaginal secretions, or a throat swab; and the method optionally includes using a spectrophotometer to measure the appearance of the refractive pattern. The most common gas that is contemplated as being used with the biosensing device of the present invention is air.

The biosensing device of the present invention utilizes methods of contact printing of patterned, antibody-binding proteins on substrates, desirably metalized polymer films, the subsequent exposure to antibody to achieve patterned antibody, the compositions produced thereby, and the use of these compositions. Patterned antibody-binding protein layers allow for the controlled placement of antibodies thereon which can bind an analyte. The term "patterned antibody-binding protein layers" as used herein means the antibody-binding protein plus the desired antibody layers in any pattern on the substrates including a solid pattern.

When the film with the patterned antibody-binding protein layers is exposed to an analyte that is capable of reacting with the antibody, the film will produce optical diffraction patterns which differ depending on the reaction of the antibody with the analyte of interest. The liquid may be a high surface tension fluid such as water. The light can be in the visible spectrum, and be either reflected from the film, or transmitted through it, and the analyte can be any compound reacting with the patterned antibody-binding protein layer.

In preferred embodiments, the method involves contacting the substrate with a test sample potentially containing the analyte under conditions in which the substrate causes a change in the refractive index. When light is transmitted through the film with the patterned antibody-binding protein layer, a visible diffraction pattern is formed and can be visualized by directing the light to a surface or by looking directly through the substrate.

In one embodiment, the present invention is contemplated in a dipstick form in which the micro-contact printed film is mounted at the end of the dipstick. In use the dipstick is dipped into the liquid in which the suspected analyte may be present and allowed to remain for several minutes. The dipstick is then removed and then, either a light is projected through the film or the film is observed with a light behind the film. If a pattern is observed, then the analyte is present in the liquid.

Figure 1:
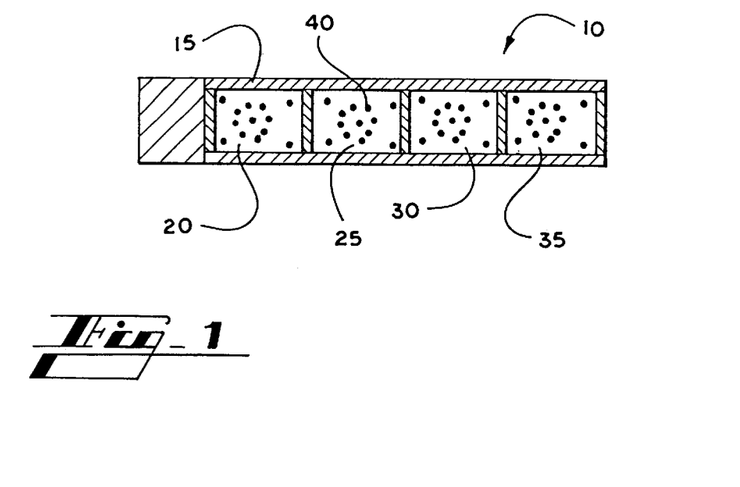
FIG. 1 shows a biosensor capable of simultaneously measuring several different analytes in a medium.

In another embodiment of the present invention, a multiple analyte test is constructed on the same support. As shown in FIG. 1, a strip 10 is provided with several micro-contact printed films 20, 25, 30 and 35, each film having a pattern 40 printed thereon. Each of the micro-contact printed metalized films 15, 20, 25, and 30 have a different antibody that is specific for different analytes. It can be seen that the present invention can be formatted in any array with a variety of micro-contact printed metalized films thereby allowing the user of the biosensor device of the present invention to detect the presence of multiple analytes in a medium using a single test.

In yet another embodiment of the present invention, the biosensor can be attached to an adhesively backed sticker or decal which can then be placed on a hard surface or container wall. The biosensor can be placed on the inside surface of a container such as a food package or a glass vial. The biosensor can then be visualized to determine the presence of analyte.

Typically, a gold film, 5 to 2000 nm thick, is supported on a titanium-primed polyethylene-terephthalate film, Si/SiO$_2$ wafer or glass sheet. The titanium serves as an adhesion promoter between gold and the support. The antibody-binding protein attaches to the gold surface during contact printing.

Figure 2:
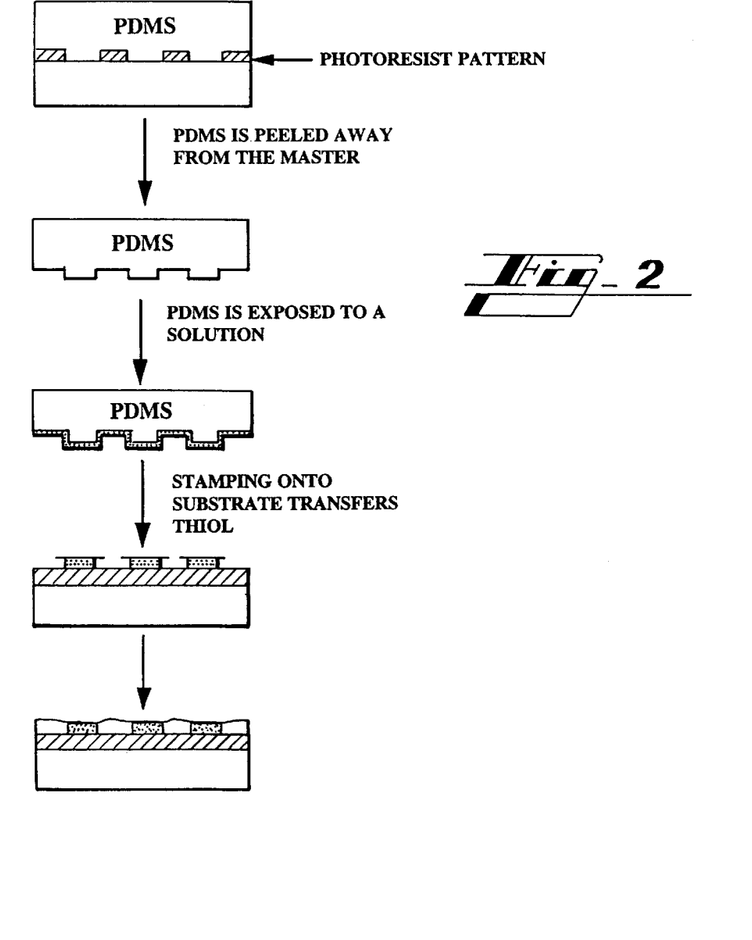
FIG. 2 is a schematic of contact printing of antibody-binding protein layers, followed by patterned deposition of an antibody.

FIG. 2 outlines the procedure used for microcontact printing. An elastomeric stamp is used to transfer antibody-binding protein "ink" to a surface by contact; if the stamp is patterned, a patterned antibody-binding protein layer forms. The stamp is fabricated by casting polydimethylsiloxane (PDMS) on a master having the desired pattern. Masters are prepared using standard photolithographic techniques, or constructed from existing materials having microscale surface features.

In a preferred embodiment of a typical experimental procedure, a photolithographically produced master is placed in a glass or plastic Petri dish, and a 10:1 ratio (w:w) mixture of SYLGARD® silicone elastomer 184 and SYLGARD® silicone elastomer 184 curing agent (Dow Corning Corporation) is poured over it. The elastomer is allowed to sit for approximately 30 minutes at room temperature and reduced pressure to degas, then cured for at least 4 hours at 60° C., and gently peeled from the master. "Inking" of the elastomeric stamp is accomplished by exposing the stamp to a 0.1 to 10 $\mu$M aqueous solution of disulfide-derivatized antibody-binding protein typically by placing the stamp face down in the solution for 10 seconds to 10 minutes. The stamp is allowed to dry, either under ambient conditions, or typically by exposure to a stream of air or nitrogen gas. Following inking, the stamp is applied to a gold surface. Light pressure is used to ensure complete contact between the stamp and the surface. After 1 second to 5 minutes, the stamp is then gently peeled from the surface. Following removal of the stamp, the surface is rinsed and dried. Alternatively, further derivatization of unstamped areas can be accomplished, either by using a second stamp or by exposing the entire surface with a different reagent. Subsequently, exposure to a protein-blocking agent, such as BSA or β-casein, or any other agent well known in the art, can also be done. After the pattern is positioned, the patterned surface would be exposed to an antibody specific for the desired analyte either by immersion in a solution or by spraying or spin coating the solution onto the patterned surface.

The elastomeric character of the stamp is important to the success of the process. Polydimethylsiloxane (PDMS), when cured, is sufficiently elastomeric to allow good conformal contact of the stamp and the surface, even for surfaces with significant relief; this contact is essential for efficient contact transfer of the protein to the gold film. The elastomeric properties of PDMS are also important when the stamp is removed from the master: if the stamp were rigid (as is the master) it would be difficult to separate the stamp and master after curing without damaging one of the two substrates. PDMS is also sufficiently rigid to retain its shape, even for features with sub-micron dimensions. The surface of PDMS has a low interfacial free energy (y=22.1 dynes/cm), and the stamp does not adhere to the gold film. The stamp is durable in that the same stamp can be used up to 100 times over a period of several months without significant degradation in performance. The polymeric nature of PDMS also plays a critical role in the inking procedure, by enabling the stamp to absorb the protein ink by swelling.

A more detailed description of the methods and compositions of the present invention follows. All publications cited herein are incorporated by reference in their entirety.

Any plastic film is suitable for the present invention. Preferably, the plastic film is also capable of having a metal coating deposited thereon. These include, but are not limited to polymers such as: polyethylene-terephthalate (MYLAR®), acrylonitrile-butadiene-styrene, acrylonitrile-methyl acrylate copolymer, cellophane, cellulosic polymers such as ethyl cellulose, cellulose acetate, cellulose acetate butyrate, cellulose propionate, cellulose triacetate, cellulose triacetate, polyethylene, polyethylene-vinyl acetate copolymers, ionomers (ethylene polymers) polyethylene-nylon copolymers, polypropylene, methyl pentene polymers, polyvinyl fluoride, and aromatic polysulfones. Preferably, the plastic film has an optical transparency of greater than 80%. Other suitable thermoplastics and suppliers may be found, for example, in reference works such as the *Modern Plastics Encyclopedia* (McGraw-Hill Publishing Co., New York 1923–1996).

In one embodiment of the invention, the polymer film has a metal coating thereon and has an optical transparency of between approximately 5% and 95%. A more desired optical transparency for the thermoplastic film used in the present invention is between approximately 20% and 80%. In a desired embodiment of the present invention, the polymer film has at least an approximately 80% optical transparency, and the thickness of the metal coating is such as to maintain an optical transparency greater than about 20%, so that diffraction patterns can be produced by either reflected or transmitted light. This corresponds to a metal coating thickness of about 10 nm. However, in other embodiments of the invention, the gold thickness may be between approximately 1 nm and 1000 nm.

The preferred metal for deposition on the film is gold. However, silver, aluminum, chromium, copper, iron, zirconium, platinum and nickel, as well as oxides of these metals, may be used.

In principle, any surface with corrugations of appropriate size could be used as masters. The process of microcontact printing starts with an appropriate relief structure, from which an elastomeric stamp is cast. This 'master' template may be generated photolithographically, or by other procedures, such as commercially available diffraction gratings. In one embodiment, the stamp may be made from polydimethylsiloxane.

In another embodiment, the invention features an optical assay device, having an optically active receptive surface configured and arranged to allow simultaneous assay of a plurality of samples on the surface for one analyte of interest, and an automated liquid handling apparatus (e.g., a pipetting device) configured and arranged to dispense sample and reagent solutions to the surface.

Below is provided an indication of the methodology by which the optimal materials and methods useful for construction of optical test surfaces of this invention can be made. Generally, the present invention includes novel optically active test surfaces for the direct detection of an analyte. These test surfaces have an analyte-specific antibody bound to the test surface by use of an attachment layer—namely the antibody-binding proteins. Thus, the present invention provides a detection device which includes selecting an optical substrate, patterning it with antibody-binding protein, and then exposing this to the antibody for the desired analyte. The detection method involves contacting this device with a sample fluid containing the analyte of interest, and then examining the change in diffraction of transmitted or reflected light by observing whether a diffraction pattern is formed.

The present invention has a broad range of applications and may be utilized in a variety of specific binding pair assay methods. For example, the devices of this invention can be used in immunoassay methods for either antigen or antibody detection. The devices may be adapted for use in direct, indirect, or competitive detection schemes.

In one embodiment of the present invention, the antibody-binding protein layer has the following general formula:

X—P—Ab

X is optional as a means of allowing chemisorption to a metal or metal oxide. For example, X may be asymmetrical or symmetrical disulfide (—R'SSY', —RSSY), sulfide (—R'SY', —RSY), diselenide (—R'Se—SeY'), selenide (—R'SeY', —RSeY), thiol (—SH), nitrile (—CN), isonitrile, nitro (—$NO_2$), selenol (—SeH), trivalent phosphorous compounds, isothiocyanate, xanthate, thiocarbamate, phosphine, thioacid or dithioacid, carboxylic acids, hydroxylic acids, and hydroxamic acids.

P represents the antibody-binding proteins which may be derivatized with X. Ab represents the antibody specific to the desired analyte.

The stamp may be applied in air, or under a fluid such as water to prevent excess diffusion of the protein material. For large-scale or continuous printing processes, it is most desirable to print in air, since shorter contact times are desirable for those processes.

In one embodiment of the present invention, the pattern is formed on the metalized thermoplastic polymer with the antibody-binding protein layer. In another embodiment of the present invention, the relief of the pattern is formed with the antibody-binding protein layer. After the stamping process, the metalized areas on the plastic may optionally be passivated or blocked, for example, with a reagent such as β-casein. Preferably this is done prior to exposure to the antibody.

This invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention.

EXAMPLES

Example 1

Antibody-conjugated polystyrene particles were produced by carbodiimide coupling with ethyldimethylaminodicarbodiimide (EDAC, bottle No. 3 of Polysciences kit, Catalog No. 19539). For this example, 0.125 mL of a 10% suspension of 0.5 micron diameter blue carboxylated particles (Bangs Laboratories; Fishers, Ind.; Cat #D0005070CB) were activated with an aqueous solution of the EDAC for 1–4 hours, rinsed, then exposed to 300 micrograms of a monoclonal antibody to luteinizing hormone, alpha subunit, (Fitzgerald Industries, Cat. No. 10-L10, Clone No. M94136). The particles were again rinsed, blocked with bovine serum albumin, and stored at 2.5% concentration in phosphate buffered saline.

A 10 mM aqueous stock solution of Sulfo-LC-SPDP (Pierce Chemical Co.; Rockford, Ill.) was prepared by dissolving 1.3 mg Sulfo-LC-SPDP into 2.07 mL de-ionized water. The conjugation reaction was carried out in phosphate buffered saline (PBS) containing 20 mM sodium phosphate buffer, 150 mM NaCl, 1 mM EDTA, and 0.02% sodium azide at pH 7.5. One milligram of lyophilized Protein A or Protein G was dissolved in 450 microliters PBS, and 50 microliters of Sulfo-LC-SPDP stock solution was added to the antibody solution. The mixture was allowed to react at room temperature for 60 minutes. The sample was applied to a 5-mL desalting polyacrylamide column previously equilibrated with 5 bed volumes (25 mL) of PBS. Fractions were eluted using PBS as the elution buffer, and the protein in the fractions was monitored using a COOMASSIE® Plus Protein Assay (Pierce Chemical Co.). Typically, 50 μL of the COOMASSIE® reagent was mixed with 50 μL of each fraction in a micro-titer plate. The COOMASSIE® reagent reacted with the protein, producing a blue color, the intensity of which was dependent upon the amount of protein present in the fraction. The fractions which produced the most intense blue color were those containing the majority of the protein eluted. These fractions were pooled together as the disulfide form of the final derivatized product. This was typically the form used for contact printing.

Optionally, the disulfide-pyridyl group present on the disulfide form of the thiolated binder can be reduced to a thiol group in a reduction reaction. Instead of desalting on a column equilibrated with PBS, the derivatized protein was desalted on a column equilibrated with an acetate buffer (100 mM sodium acetate buffer, 100 mM NaCl, pH 4.5). The acidic pH of this acetate buffer acts to protect any disulfide bonds present on the native protein from undesired reduction. In the reduction reaction, 12 mg of dithiothreitol (DTT) is dissolved in 500 mL acetate buffer and added to 1 mL of the SPDP derivatized protein. The reaction mixture was incubated for 30 minutes at room temperature, and desalted on a 5 mL desalting column equilibrated with 5 bed volumes (25 mL) of acetate buffer. The protein content of the fractions eluted was again monitored by the COOMASSIE® Protein Assay reagent as described above, and the fractions containing the greatest amount of protein were pooled for subsequent contact printing.

Both the disulfide and reduced forms of the thiolated binders were stored in aqueous solution at 4° C. until used for contact printing.

A gold/MYLAR® film was pre-treated (or blocked) with a 5 mg/mL beta casein solution for 10 minutes, then thoroughly rinsed and dried under an air stream. A PDMS stamp of 10-micron circles was coated with thiolated antibody-binding protein by placing the stamp face down in a 0.5 mg/mL thiolated Protein A (or Protein G) solution and soaking for 10 minutes. A strong air stream was used to thoroughly dry the surface of the stamp. The coated stamp is placed in contact with the gold/MYLAR® for 5 minutes, then removed. The resulting printed gold/MYLAR® was rinsed in distilled water, and dried.

The sensor was then exposed to an antibody solution (e.g., a 2 ug/mL PBS solution of monoclonal antibody to luteinizing hormone-beta, Catalog No. 10-L15, Clone No. M94187, Fitzgerald Industries International, Inc.; Concord, Mass.) for 30 minutes, followed by rinsing, and air-drying.

The sensor sample was exposed to a 2 ug/mL aqueous solution (with 1% bovine serum albumin) of goat anti-mouse HRP (horse radish peroxidase labeled) by placing a droplet of the solution on top of the sensor surface for 30–60 minutes at room temperature. The sample was rinsed with 0.02% Tween 20 solution, then distilled water. A subsequent exposure to a TMB membrane enhancer solution (e.g., a 10:1 v/v mixture of Kirkegaard and Perry Laboratories' reagents Cat No. 50-7618 and Cat. No. 50-77-01) was done by placing the TMB solution on the sensor sample for 10 minutes. This caused the development of a blue precipitate in the circles or features, as well as a diffraction image to form upon irradiation with a point light source.

Optionally, the analyte solution (e.g., luteinizing hormone for this example) is mixed with microparticles (typically 50–70 microliters of analyte solution with 10–20 microliters of 1.5–2.5% antibody-conjugated particle suspension), and placed on top of the sensor (typically a 1 cm square sensor sample is used). After 5–10 minutes, a nitrocellulose disk (5 or 8 micron pore size, Sigma No. N3771 or N4146) with a small hole punched out of the center is placed on top of the sensor. This acts to wick away excess fluid and unbound microparticles. At that time, a point light source is transmitted through the sensor sample (using the small hole in the nitrocellulose). If the analyte was present, then a diffraction image is seen on the other side of the light beam.

Example 2

Antibody-conjugated polystyrene particles were produced by carbodiimide coupling with ethyldimethylaminodicarbodiimide (EDAC, bottle No. 3 of Polysciences kit, Catalog No. 19539). For this example, 0.125 mL of a 10% suspension of 0.5 micron diameter blue carboxylated particles (Bangs Laboratories; Fishers, Ind.; Cat. No. D0005070CB) were activated with an aqueous solution of the EDAC for 1–4 hours, rinsed, then exposed to 300 micrograms of a polyclonal antibody to IgE (such as chicken anti-IgE in order to be unreactive to the patterned Protein A). The particles were again rinsed, blocked with bovine serum albumin, and stored at 2.5% concentration in phosphate buffered saline.

A 10 mM aqueous stock solution of Sulfo-LC-SPDP (Pierce Chemical Co.; Rockford, Ill.) was prepared by dissolving 1.3 mg Sulfo-LC-SPDP into 2.07 mL de-ionized water. The conjugation reaction was carried out in phosphate buffered saline (PBS) containing 20 mM sodium phosphate buffer, 150 mM NaCl, 1 mM EDTA, and 0.02% sodium azide at pH 7.5. One milligram of lyophilized Protein A was dissolved in 450 microliters PBS, and 50 microliters of Sulfo-LC-SPDP stock solution was added to the antibody solution. The mixture was allowed to react at room temperature for 60 minutes. The sample was applied to a 5-mL desalting polyacrylamide column previously equilibrated with 5 bed volumes (25 mL) of PBS. Fractions were eluted using PBS as the elution buffer, and the protein in the fractions were monitored using a COOMASSIE® Plus Protein Assay (Pierce Chemical Co.). Typically, 50 µL of the COOMASSIE® reagent was mixed with 50 µL of each fraction in a micro-titer plate. The COOMASSIE® reagent reacted with the protein, producing a blue color, the intensity of which was dependent upon the amount of protein present in the fraction. The fractions which produced the most intense blue color were those containing the majority of the protein eluted. These fractions were pooled together as the disulfide form of the final derivatized product. This was typically the form used for contact printing.

Optionally, the disulfide-pyridyl group present on the disulfide form of the thiolated binder can be reduced to a thiol group in a reduction reaction. Instead of desalting on a column equilibrated with PBS, the derivatized protein was desalted on a column equilibrated with an acetate buffer (100 mM sodium acetate buffer, 100 mM NaCl, pH 4.5). The acidic pH of this acetate buffer acts to protect any disulfide bonds present on the native protein from undesired reduction. In the reduction reaction, 12 mg of dithiothreitol (DTT) was dissolved in 500 mL acetate buffer and added to 1 mL of the SPDP derivatized protein. The reaction mixture was incubated for 30 minutes at room temperature, and desalted on a 5 mL desalting column equilibrated with 5 bed volumes (25 mL) of acetate buffer. The protein content of the fractions eluted was again monitored by the COOMASSIE® Protein Assay reagent as described above, and the fractions containing the greatest amount of protein were pooled for subsequent contact printing.

Both the disulfide and reduced forms of the thiolated binders were stored in aqueous solution at 4*C until used for contact printing.

A gold/MYLAR® film was pre-treated (or blocked) with a 5 mg/mL beta casein solution for 10 minutes, then thoroughly rinsed and dried under an air stream. A PDMS stamp of 10-micron circles was coated with thiolated antibody-binding protein by placing the stamp face down in a 0.5 mg/mL thiolated Protein A solution and soaking for 10 minutes. A strong air stream was used to thoroughly dry the surface of the stamp. The coated stamp was placed in contact with the gold/MYLAR® for 5 minutes, then removed. The resulting printed gold/MYLAR® was rinsed in distilled water, and dried.

The analyte solution (typically 50–70 microliters at 2 µg/mL PBS solution of IgE (Catalog No. 30-AI05, Fitzgerald Industries International, Inc.; Concord, Mass.) is placed on top of the sensor (typically a 1 cm square) for 0–20 minutes, followed by 10–20 microliters of 1.5–2.5% antibody-conjugated particle suspension for an additional 5–20 minutes. A nitrocellulose disk (5 or 8 micron pore size, Sigma No. N3771 or N4146) with a small hole punched out of the center is then placed on top of the sensor. This acts to wick away excess fluid and unbound microparticles. At that time, a point light source is transmitted through the sensor sample (using the small hole in the nitrocellulose). If the analyte was present, then a diffraction image is seen on the other side of the light beam, as illustrated.

We claim:
1. A biosensor consisting of:
   a polymer film; and
   antibody-binding protein layer printed in a pattern onto the polymer film wherein the antibody-binding protein layer has an antibody thereon that is specific for an analyte, wherein the antibody binding protein layer is printed directly onto the polymer film;
   further wherein the protein layer is printed in a pattern such that when the biosensor binds an analyte, the biosensor diffracts transmitted light or reflected light to form a diffraction pattern.
2. The biosensor of claim 1, wherein the antibody-binding protein layer is printed in a pattern such that when the biosensor binds the analyte, the biosensor diffracts transmitted light to form a diffraction pattern.

3. The biosensor of claim 2, wherein the diffraction pattern is visible with an unaided eye.

4. The biosensor of claim 1, wherein the polymer film further comprises a metal coating.

5. The biosensor of claim 4, wherein the metal is selected from the group consisting of gold, silver, chromium, nickel, platinum, aluminum, iron, copper, zirconium, and oxides thereof.

6. The biosensor of claim 4, wherein the metal is gold.

7. The biosensor of claim 6, wherein the gold coating is between approximately 1 nanometer and 1000 nanometers in thickness.

8. The biosensor of claim 1, wherein the polymer film is selected from the group consisting of polyethylene-terephthalate, acrylonitrile-butadiene-styrene, acrylonitrile-methyl acrylate copolymer, cellophane, cellulosic polymers such as ethyl cellulose, cellulose acetate, cellulose acetate butyrate, cellulose propionate, cellulose triacetate, cellulose triacetate, polyethylene, polyethylene-vinyl acetate copolymers, ionomers (ethylene polymers) polyethylene-nylon copolymers, polypropylene, methyl pentene polymers, polyvinyl fluoride, and aromatic polysulfones.

9. The biosensor of claim 8, wherein the polymer film is polyethylene-terephthalate.

10. The biosensor of claim 1, wherein the polymer film is optically transparent.

11. The biosensor of claim 1, wherein the polymer film has an optical transparency between 5% and 95%.

12. The biosensor of claim 1, wherein the polymer film has an optical transparency between approximately 20% and 80%.

13. The biosensor of claim 1, wherein the antibody-binding protein layer is formed from compounds with the following general formula:

wherein:

X is reactive with the metal or metal oxide on the polymer film;

P is an antibody-binding protein; and

Ab is an antibody specific to a desired analyte.

14. The biosensor of claim 13, wherein:

X is a asymmetrical or symmetrical disulfide (—SSY', —SSY), sulfide (—'SY', SY), diselenide (—'Se—SeY'), selenide (—SeY', —SeY), thiol (—SH), nitrile (—CN), isonitrile, nitro (—NO$_2$), selenol (—SeH), trivalent phosphorous compounds, isothiocyanate, xanthate, thiocarbamate, phosphine, thioacid or dithioacid, carboxylic acids, hydroxylic acids, and hydroxamic acids.

15. The biosensor of claim 1, wherein the analyte is selected from the group consisting of bacteria, yeast, fungus, virus, rheumatoid factor, IgG, IgM, IgA and IgE antibodies, carcinoembryonic antigen, streptococcus Group A antigen, viral antigens, antigens associated with autoimmune disease, allergens, tumor antigens, streptococcus Group B antigen, HIV I or HIV II antigen, antibodies, viruses, antigens specific to RSV, antigen, enzyme, hormone, polysaccharide, protein, lipid, carbohydrate, drug, nucleic acid, *Neisseria meningitides* groups A, B, C, Y and W sub 135, *Streptococcus pneumoniae, E. coli* K1, *Haemophilus influenza* type B, an antigen derived from microorganisms, a hapten, a drug of abuse, a therapeutic drug, an environmental agent, and antigens specific to hepatitis.

16. The biosensor of claim 15, wherein the analyte is bacteria, yeast, fungus or virus.

17. The biosensor of claim 16, wherein the fungus is Candida species.

18. The biosensor of claim 16, wherein the bacteria is Salmonella species.

19. The biosensor of claim 1, wherein the antibody-binding protein layer is selected from the group consisting of Protein A, Protein G, Protein L, and a recombinant form thereof.

20. A method of making a biosensor consisting of printing a pattern of antibody-binding protein layer directly onto a polymer film wherein the antibody-binding protein layer has an antibody thereon, further wherein the protein layer is printed in a pattern such that when the biosensor binds an analyte, the biosensor diffracts transmitted light or reflected light to form a diffraction pattern.

21. The method of claim 20, wherein the antibody-binding protein layer is printed in a pattern such that when the biosensor binds an analyte, the biosensor diffracts transmitted light to form a diffraction pattern.

22. The method of claim 20, wherein the polymer film further comprises a metal coating.

23. The method of claim 22, wherein the metal is selected from the group consisting of gold, silver, chromium, nickel, platinum, aluminum, iron, copper, zirconium, and oxides thereof.

24. The method of claim 22, wherein the metal is gold.

25. The method of claim 24, wherein the gold coating is between approximately 1 nanometer and 1000 nanometers in thickness.

26. The method of claim 20, wherein the polymer film is selected from the group consisting of polyethylene-terephthalate, acrylonitrile-butadiene-styrene, acrylonitrile-methyl acrylate copolymer, cellophane, cellulosic polymers such as ethyl cellulose, cellulose acetate, cellulose acetate butyrate, cellulose propionate, cellulose triacetate, cellulose triacetate, polyethylene, polyethylene-vinyl acetate copolymers, ionomers (ethylene polymers) polyethylene-nylon copolymers, polypropylene, methyl pentene polymers, polyvinyl fluoride, and aromatic polysulfones.

27. The method of claim 26, wherein the polymer film is polyethylene-terephthalate.

28. The method of claim 20, wherein the polymer film is optically transparent.

29. The method of claim 28, wherein the polymer film has an optical transparency between 5% and 95%.

30. The method of claim 28, wherein the polymer film has an optical transparency between approximately 20% and 80%.

31. The method of claim 20, wherein the antibody-binding protein layer is formed from compounds with the following general formula:

wherein:

X is reactive with the metal or metal oxide on the polymer film;

P is an antibody-binding protein; and

Ab is an antibody specific to a desired analyte.

32. The method of claim 31, wherein:

X is a asymmetrical or symmetrical disulfide (—SSY', —SSY), sulfide (—'SY', SY), diselenide (—'Se—SeY'), selenide (—SeY', —SeY), thiol (—SH), nitrile (—CN), isonitrile, nitro (—NO$_2$), selenol (-SeH), trivalent phosphorous compounds, isothiocyanate, xanthate, thiocarbamate, phosphine, thioacid or dithioacid, carboxylic acids, hydroxylic acids, and hydroxamic acids.

33. The method of claim 20, wherein the analyte is selected from the group consisting of bacteria, yeast, fungus, virus, rheumatoid factor, IgG, IgM, IgA and IgE antibodies, carcinoembryonic antigen, streptococcus Group A antigen, viral antigens, antigens associated with autoimmune disease, allergens, tumor antigens, streptococcus Group B antigen, HIV I or HIV II antigen, antibodies, viruses, antigens specific to RSV, antigen, enzyme, hormone, polysaccharide, protein, lipid, carbohydrate, drug, nucleic acid, *Neisseria meningitides* groups A, B, C, Y and W sub 135, *Streptococcus pneumoniae, E. coli* K1, *Haemophilus influenza* type B, an antigen derived from microorganisms, a hapten, a drug of abuse, a therapeutic drug, an environmental agent, and antigens specific to hepatitis.

34. The method of claim 33, wherein the analyte is bacteria, yeast, fungus or virus.

35. The method of claim 20, wherein the antibody-binding protein layer is selected from the group consisting of Protein A, Protein G, Protein L, and a recombinant form thereof.

36. A biosensor consisting of:
   a polymer film; and
   an antibody-binding protein layer printed in a pattern onto the polymer film wherein the antibody-binding protein layer is capable of acting as a receptor for an analyte, wherein the antibody binding protein layer is printed directly onto the polymer film.

37. The biosensor of claim 36, wherein the antibody-binding protein layer is printed in a pattern such that when the biosensor binds the analyte, the biosensor diffracts transmitted light to form a diffraction pattern.

38. The biosensor of claim 37, wherein the diffraction pattern is visible with an unaided eye.

39. The biosensor of claim 36, wherein the polymer film further comprises a metal coating.

40. The biosensor of claim 39, wherein the metal is selected from the group consisting of gold, silver, chromium, nickel, platinum, aluminum, iron, copper, zirconium, and oxides thereof.

41. The biosensor of claim 39, wherein the metal is gold.

42. The biosensor of claim 41, wherein the gold coating is between approximately 1 nanometer and 1000 nanometers in thickness.

43. The biosensor of claim 36, wherein the polymer film is selected from the group consisting of polyethylene-terephthalate, acrylonitrile-butadiene-styrene, acrylonitrile-methyl acrylate copolymer, cellophane, cellulosic polymers such as ethyl cellulose, cellulose acetate, cellulose acetate butyrate, cellulose propionate, cellulose triacetate, cellulose triacetate, polyethylene, polyethylene-vinyl acetate copolymers, ionomers (ethylene polymers) polyethylene-nylon copolymers, polypropylene, methyl pentene polymers, polyvinyl fluoride, and aromatic polysulfones.

44. The biosensor of claim 43, wherein the polymer film is polyethylene-terephthalate.

45. The biosensor of claim 36, wherein the polymer film is optically transparent.

46. The biosensor of claim 36, wherein the polymer film has an optical transparency between 5% and 95%.

47. The biosensor of claim 36, wherein the polymer film has an optical transparency between approximately 20% and 80%.

48. The biosensor of claim 36, wherein the antibody-binding protein layer is formed from compounds with the following general formula:

$$X-P$$

wherein:

X is reactive with the metal or metal oxide on the polymer film;

P is an antibody-binding protein.

49. The biosensor of claim 48, wherein:

X is a asymmetrical or symmetrical disulfide (—SSY', —SSY), sulfide (—'SY', SY), diselenide (—'Se—SeY'), selenide (—SeY', —SeY), thiol (—SH), nitrile (—CN), isonitrile, nitro (—NO$_2$), selenol (—SeH), trivalent phosphorous compounds, isothiocyanate, xanthate, thiocarbamate, phosphine, thioacid or dithioacid, carboxylic acids, hydroxylic acids, and hydroxamic acids.

50. The biosensor of claim 36, wherein the analyte is selected from antibodies such as IgG, IgM, IgA and IgE.

51. The biosensor of claim 36, wherein the protein material is selected from the group consisting of Protein A, Protein G, Protein L, and a recombinant form thereof.

52. The biosensor of claim 36, further comprising a diffraction enhancing element, wherein the diffraction enhancing element includes an antibody that is capable of binding to the analyte.

* * * * *